(12) United States Patent
Gunderson et al.

(10) Patent No.: US 9,839,784 B2
(45) Date of Patent: Dec. 12, 2017

(54) IDENTIFYING LEAD INSULATION BREACHES AND EXTERNALIZATION OF LEAD CONDUCTORS

(71) Applicant: Medtronic, Inc., Minneapolis, MN (US)

(72) Inventors: Bruce D. Gunderson, Plymouth, MN (US); Walter H. Olson, North Oaks, MN (US); ShaileshKumar V. Musley, Blaine, MN (US); Jennifer P. Miller, Elk River, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/803,302

(22) Filed: Mar. 14, 2013

(65) Prior Publication Data
US 2013/0304160 A1    Nov. 14, 2013

Related U.S. Application Data

(60) Provisional application No. 61/644,077, filed on May 8, 2012.

(51) Int. Cl.
*A61N 1/372*    (2006.01)
*A61N 1/08*    (2006.01)

(52) U.S. Cl.
CPC .............. *A61N 1/372* (2013.01); *A61N 1/08* (2013.01); *A61N 2001/083* (2013.01); *F04C 2270/041* (2013.01)

(58) Field of Classification Search
CPC ................................................ A61N 2001/083

USPC .......................................................... 607/66
See application file for complete search history.

(56) References Cited

U.S. PATENT DOCUMENTS

| | | | |
|---|---|---|---|
| 4,825,869 A | 5/1989 | Sasmor et al. |
| 4,899,750 A | 2/1990 | Ekwall |
| 5,215,081 A | 6/1993 | Ostroff |
| 5,549,646 A | 8/1996 | Katz |

(Continued)

FOREIGN PATENT DOCUMENTS

| | | |
|---|---|---|
| CN | 101628151 A | 1/2010 |
| EP | 0437104 A2 | 7/1991 |

(Continued)

OTHER PUBLICATIONS (PCT/US2013/040084) PCT Notification of Transmittal of the International Search Report and the Written Opinion of the International Searching Authority, 7 pages.

(Continued)

*Primary Examiner* — Joseph Dietrich

(57) ABSTRACT

A technique for identifying lead-related conditions, such as insulation breaches and/or externalization of lead conductors, includes analyzing characteristics of electrical signals generated on one or more electrode sensing vectors of the lead by a test signal to determine whether a lead-related condition exists. The characteristics of the electrical signals induced on the lead by the test signal may be significantly different on a lead having an insulation breach or externalized conductor than on a lead not having such lead-related conditions. As such, the implantable medical device may be subject to a known test signal and analyze the signals on the lead to detect lead-related conditions.

26 Claims, 7 Drawing Sheets

(56) References Cited

U.S. PATENT DOCUMENTS

| | | | |
|---|---|---|---|
| 5,741,311 | A | 4/1998 | McVenes et al. |
| 5,755,742 | A | 5/1998 | Schuelke et al. |
| 5,814,088 | A | 9/1998 | Paul et al. |
| 5,897,577 | A | 4/1999 | Cinbis et al. |
| 5,944,746 | A | 8/1999 | Kroll |
| 7,844,329 | B2 | 11/2010 | Chambers |
| 7,970,472 | B2 | 6/2011 | Ricke et al. |
| 8,170,677 | B2 | 5/2012 | Chambers et al. |
| 8,634,918 | B2 | 1/2014 | Chambers |
| 2002/0120307 | A1 | 8/2002 | Jorgenson et al. |
| 2003/0105500 | A1 | 6/2003 | Anderson et al. |
| 2004/0064161 | A1 | 4/2004 | Gunderson et al. |
| 2005/0096719 | A1 | 5/2005 | Hammill et al. |
| 2005/0137636 | A1 | 6/2005 | Gunderson et al. |
| 2005/0177199 | A1 | 8/2005 | Hansen |
| 2006/0116730 | A1 | 6/2006 | Gunderson |
| 2006/0247706 | A1 | 11/2006 | Germanson et al. |
| 2007/0027676 | A1 | 2/2007 | Chambers et al. |
| 2007/0100407 | A1 | 5/2007 | Armstrong |
| 2007/0255352 | A1 | 11/2007 | Roline et al. |
| 2007/0293903 | A1 | 12/2007 | Bohn et al. |
| 2008/0161870 | A1 | 7/2008 | Gunderson |
| 2008/0255630 | A1 | 10/2008 | Arisso |
| 2009/0125079 | A1 | 5/2009 | Armstrong |
| 2009/0157337 | A1 | 6/2009 | Zhang et al. |
| 2009/0259216 | A1 | 10/2009 | Drew et al. |
| 2009/0299201 | A1 | 12/2009 | Gunderson |
| 2009/0299432 | A1 | 12/2009 | Stadler et al. |
| 2010/0023084 | A1 | 1/2010 | Gunderson |
| 2010/0087891 | A1 | 4/2010 | Levine et al. |
| 2010/0106209 | A1 | 4/2010 | Gunderson et al. |
| 2010/0114204 | A1* | 5/2010 | Burnes et al. .............. 607/4 |
| 2010/0114222 | A1* | 5/2010 | Gunderson ............. A61N 1/37 607/8 |
| 2010/0228307 | A1 | 9/2010 | Kroll et al. |
| 2011/0009918 | A1 | 1/2011 | Bornzin et al. |
| 2011/0098765 | A1 | 4/2011 | Patel |
| 2011/0184481 | A1 | 7/2011 | Hoeppner et al. |
| 2011/0270355 | A1 | 11/2011 | Chambers |
| 2012/0004699 | A1 | 1/2012 | Bobgan et al. |
| 2012/0109246 | A1 | 5/2012 | Seifert et al. |
| 2012/0191153 | A1 | 7/2012 | Swerdlow et al. |
| 2012/0197365 | A1* | 8/2012 | Germanson .......... A61N 1/0563 607/116 |
| 2012/0316621 | A1 | 12/2012 | Spear et al. |
| 2013/0013038 | A1 | 1/2013 | Miller |
| 2013/0041444 | A1 | 2/2013 | Foster et al. |
| 2013/0304139 | A1 | 11/2013 | Musley et al. |
| 2013/0304160 | A1 | 11/2013 | Gunderson et al. |

FOREIGN PATENT DOCUMENTS

| | | |
|---|---|---|
| WO | 2007059386 A2 | 5/2007 |
| WO | 2010034080 A1 | 4/2010 |
| WO | 2010051388 A1 | 5/2010 |

OTHER PUBLICATIONS

Lakshmanados, Umashankar et al.; "Electromagnetic Interference of Pacemakers"; Modern Pacemakers—Present and Future; Chapter 13; Published online Feb. 14, 2011; pp. 229-252.

Hokkaido University, Japan; "Investigation of Implantable Medical Device EMI Due to Radio Waves from RFID reader/writers"; ISO WG4 SG5 Meeting, 2006; 39 pages.

Olson, Walter H.; "Electrical Safety"; Medical Instrumentation Application and Design, 4thEdition, Chapter 14; Editor John G. Webster, Feb. 2009; pp. 638-675.

Dawson, Trevor W. et al.; "Pacemaker Interference by 60-Hz Contact Currents"; IEEE Transactions on Biomedical Engineering; vol. 49, No. 8, Aug. 2002; pp. 878-886.

First Office Action, and translation thereof, from counterpart Chinese Patent Application No. 201380024313.4, dated Jul. 28, 2015, 9 pages.

Musley et al., "Implantable Medical System With Means for Determining Whether a Lead-Related Condition Exists", CN Patent Application No. 201380024313.4, Notice of Grant of Patent Right for Invention, Date of Dispatch, Oct. 27, 2016, in Chinese with English Translation, 8 pages.

\* cited by examiner

IDENTIFYING LEAD INSULATION BREACHES AND EXTERNALIZATION OF LEAD CONDUCTORS

This application claims the benefit of U.S. Provisional Application No. 61/644,077, filed on May 8, 2012, the entire content of which is incorporated herein by reference in its entirety.

TECHNICAL FIELD

The disclosure relates to implantable medical systems that include one or more leads to sense electrical signals within a patient and/or deliver electrical signals to a patient and, more particularly, to identifying lead related conditions of one or more leads of the system.

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscle, nerve, brain, stomach or other organs or tissues. Some therapies include the delivery of electrical stimulation to such organs or tissues. Some medical devices may employ one or more elongated electrical leads carrying electrodes for the delivery of electrical stimulation to such organs or tissues, electrodes for sensing electrical signals within the patient, which may be generated by such organs or tissue, and/or other sensors for sensing physiological parameters of a patient.

Medical leads may be configured to allow electrodes or other sensors to be positioned at desired locations for delivery of electrical stimulation or sensing. For example, electrodes or sensors may be carried at a distal portion of a lead. A proximal portion of the lead may be coupled to a medical device housing, which may contain circuitry such as stimulation generation and/or sensing circuitry. In some cases, the medical leads and the medical device housing are implantable within the patient. Medical devices with a housing configured for implantation within the patient may be referred to as implantable medical devices.

Implantable cardiac pacemakers or cardioverter-defibrillators, for example, provide therapeutic electrical stimulation to the heart via electrodes carried by one or more implantable medical leads. The electrical stimulation may include signals such as pulses or shocks for pacing, cardioversion or defibrillation. In some cases, a medical device may sense intrinsic depolarizations of the heart, and control delivery of stimulation signals to the heart based on the sensed depolarizations. Upon detection of an abnormal rhythm, such as bradycardia, tachycardia or fibrillation, an appropriate electrical stimulation signal or signals may be delivered to restore or maintain normal sinus rhythm. For example, in some cases, an implantable medical device may deliver pacing pulses to the heart of the patient upon detecting tachycardia or bradycardia, and deliver cardioversion or defibrillation shocks to the heart upon detecting fibrillation.

Implantable medical leads typically include a lead body containing one or more elongated electrical conductors that extend through the lead body from a connector assembly provided at a proximal end of the lead end to one or more electrodes located at the distal lead end or elsewhere along the length of the lead body. The conductors connect to the stimulation and/or sensing circuitry within an associated implantable medical device housing to respective electrodes or sensors. Some electrodes may be used for both stimulation and sensing. Each electrical conductor is typically electrically isolated from other electrical conductors and is encased within an outer sheath that electrically insulates the lead conductors from body tissue and fluids.

Medical lead bodies implanted transvenously within the heart tend to be continuously flexed by the beating of the heart. Medical lead bodies implanted within the heart or outside of the heart (e.g., subcutaneously) may be subject to other stresses. For example, stress may be applied to the lead body, including the conductors therein, during implantation or lead repositioning. As another example, patient movement can cause the route traversed by the lead body to be constricted or otherwise altered, causing stresses on the lead body and conductors. Even without stresses, lead insulation materials or joints may degrade inside the human body. In rare instances, such stresses or degradations may cause an insulation breach of the lead body and, in some instances, externalization of one or more of the conductors of the lead.

Lead insulation breach and/or externalization of lead conductors as well as other lead related conditions may result in undesirable operation. In the case of cardiac leads, sensing of an intrinsic heart rhythm through a lead can be altered by lead related conditions. Identification of lead related conditions may allow modifications of the stimulation therapy or sensing, or lead replacement.

SUMMARY

This disclosure describes techniques for identifying lead-related conditions, such as insulation breaches and/or externalization of lead conductors, using one or more test signals generated by a signal generator. The techniques include analyzing one or more characteristics of electrical signals generated on one or more electrode sensing vectors of an implanted lead by the test signals to determine whether a lead-related condition exists. The characteristics of the electrical signals induced on the lead by the test signals may be significantly different on a lead having an insulation breach or externalized conductor than on a lead not having such lead-related conditions. As such, the implantable medical device may be subject to a known test signal and analyze the signals on the lead to detect lead-related conditions.

In one example, the disclosure is directed to a medical device system comprising an external system having at least two electrodes configured to contact a body of a patient and a signal generator electrically coupled to the at least two electrodes. The signal generator is configured to generate a first electrical signal to be delivered by at least two electrodes. The medical device system also includes an implantable medical system including an implantable medical device and at least one implantable medical lead coupled to the implantable medical device, wherein the implantable medical system senses a second electrical signal induced on the at least one implantable medical lead by the first electrical signal generated by the signal generator. The medical system also includes a processor configured to analyze the second electrical signal sensed on the at least one implantable medical lead to determine whether a lead-related condition exists.

In another example, the disclosure is directed to a method that includes providing a first electrical signal generated by an external signal generator to a body of a patient via a pair of electrodes in contact with the body of the patient, sensing a second electrical signal induced on at least one implantable medical lead by the first electrical signal generated by the signal generator, and analyzing the second electrical signal sensed on the at least one implantable medical lead to determine whether a lead-related condition exists.

In a further example, the disclosure is directed to a medical device system that includes means for generating a first electrical signal to be delivered to a body of a patient via a pair of electrodes in contact with the body of the patient, means for sensing a second electrical signal induced on at least one implantable medical lead by the first electrical signal, and means for analyzing the second electrical signal sensed on the at least one implantable medical lead to determine whether a lead-related condition exists.

In another example, the disclosure is directed to an implantable medical system that includes at least one implantable medical lead and an implantable medical device coupled to the at least one implantable medical lead. The implantable medical device includes a signal generator configured to deliver a test signal and a processor configured to obtain an electrical signal generated on the lead by delivery of the test signal and analyze the electrical signal to determine whether a lead-related condition exists.

In a further example, the disclosure is directed to a method that includes delivering a test signal via a pair of electrodes implanted within a body of a patient, sensing an electrical signal induced on at least one implantable medical lead by the test signal, and analyzing the electrical signal sensed on the at least one implantable medical lead to determine whether a lead-related condition exists.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
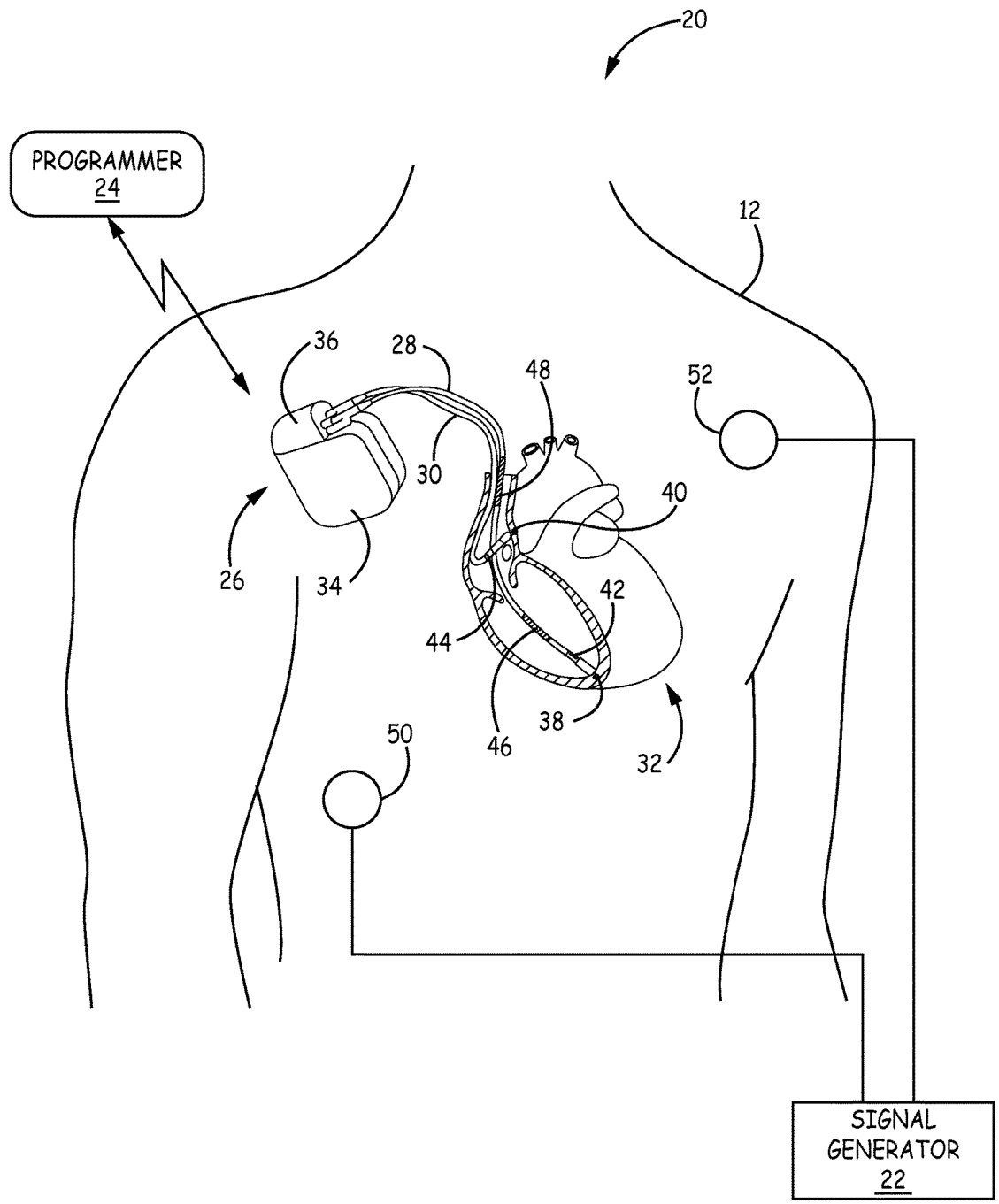
FIG. 1 is a conceptual diagram of an example medical system.

FIG. 1 is a conceptual diagram of an example medical system 20. Medical system 20 includes an IMD 26 connected to leads 28 and 30, e.g., via a connector assembly 36. Housing 34 and connector assembly 36 of IMD 26 may form a hermetic seal that protects components of IMD 26. In some examples, housing 34 may comprise a metal or other biocompatible enclosure. Connector assembly 36 may include electrical feedthroughs, through which electrical connections are made between conductors within leads 28 and 30 and electronic components included within housing 34. As will be described in further detail herein, housing 34 may house one or more processors, memories, transmitters, receivers, sensors, sensing circuitry, therapy circuitry and other appropriate components. Housing 34 is configured to be implanted in a patient, such as patient 12.

Leads 28 and 30 include a lead body that includes one or more electrodes located near the distal lead end or elsewhere along the length of the lead body. The lead bodies of leads 28 and 30 also contain one or more elongated electrical conductors (not illustrated in FIG. 1) that extend through the lead body from connector assembly 36 provided at a proximal lead end to one or more electrodes of leads 28 and 30. The lead bodies of leads 28 and 30 may be formed from a non-conductive material, including silicone, polyurethane, fluoropolymers, mixtures thereof, and other appropriate materials, and shaped to form one or more lumens within which the one or more conductors extend. However, the techniques are not limited to such constructions. Lead bodies may, in some instances, be constructed of a combination of insulating materials and conductive or semi-conductive materials (such as conductive polymers).

Leads 28 and 30 may sense electrical signals attendant to the depolarization and repolarization of heart and deliver electrical stimulation therapy via the conductors and electrodes. In the example illustrated in FIG. 1, leads 28 and 30 each include a respective tip electrodes 38 and 40 and ring electrodes 42 and 44 located near a distal end of the lead bodies of their respective leads 28 and 30. When implanted, tip electrodes 38 and 40 and/or ring electrodes 42 and 44 are placed relative to or in a selected tissue, muscle, nerve or other location within the patient 12. In the example illustrated in FIG. 1, tip electrodes 38 and 40 are extendable helically shaped electrodes to facilitate fixation of the distal end of leads 28 and 30 to the target location within patient 12. In this manner, tip electrodes 38 and 40 are formed to define a fixation mechanism. In other embodiments, one or both of tip electrodes 38 and 40 may be formed to define fixation mechanisms of other structures. In other instances, leads 28 and 30 may include a fixation mechanism separate from tip electrode 38 and 40, as in the case of passive fixation leads. Fixation mechanisms can be any appropriate type, including a grapple mechanism, a helical or screw mechanism, a drug-coated connection mechanism in which the drug(s) serves to reduce infection and/or swelling of the tissue, or other attachment mechanism.

In the example illustrated in FIG. 1, lead 28 also includes elongated defibrillation electrodes 46 and 48, which may take the form of a coil. Defibrillation electrode 46 may be an RV coil and defibrillation electrode 48 may be an SVC coil. In other instances, leads 28 and 30 may include more or fewer electrodes. For example, lead 30 may include one or more elongated defibrillation electrodes similar to those illustrated for lead 28. As another example, lead 28 may include only a single elongated defibrillation electrode. Moreover, medical system 20 may also include more or fewer leads. For example, IMD 26 may be coupled to additional leads such as a left ventricular (LV) coronary sinus lead that extends into the coronary sinus to a region adjacent to the free wall of the left ventricle of the heart.

Furthermore, in some examples, medical system 20 may additionally or alternatively include temporary or permanent epicardial or subcutaneous leads, instead of or in addition to transvenous, intracardiac leads 28 and 30.

The one or more elongated electrical conductors contained within the lead bodies of leads 28 and 30 may engage with respective ones of electrodes 38, 40, 42, 44, 46, and 48. In one example, each of electrodes 38, 40, 42, 44, 46, and 48 is electrically coupled to a respective conductor within its associated lead body. The respective conductors may electrically couple to circuitry, such as a therapy module or a sensing module, of IMD 26 via connections in connector assembly 36, including associated feedthroughs. The electrical conductors transmit therapy from a therapy module within IMD 26 to one or more of electrodes 38, 40, 42, 44, 46, and 48 and transmit sensed electrical signals from one or more of electrodes 38, 40, 42, 44, 46, and 48 to the sensing module within IMD 26. In some examples, housing 34 may function as a further electrode, sometimes referred to as a "can electrode" for use in therapy delivery and/or sensing, such as in the case of unipolar sensing or pacing or for defibrillation therapy.

The one or more electrical conductors of leads 28 and 30 may include a conductive core surrounded by an outer insulation material. The conductive core may include one or more conductive filars, which may be made from any of a variety of conductive materials, such as tantalum, platinum, silver, or any other conductive material, or a combination of conductive materials, including alloys (such as nickel-cobalt-chromium-molybdenum alloy). The outer insulation material surrounding the conductive core may be made from any of a number of non-conductive materials, such as ethylene tetrafluroethylene (ETFE), polytetrafluroethylene (PTFE), soluble imide (SI), parylene, tantalum pentoxide, polyether ether ketone (PEEK), liquid crystal polymer (LCP), perfluoroalkoxy (PFA), fluorinated ethylene propylene (FEP), urethanes, or other non-conductive material or combination of non-conductive materials. In some instances, conductive cores may have no outer insulation.

In the example illustrated in FIG. 1, system 20 is an implantable cardiac system, such as implantable pacemaker system, implantable cardioverter defibrillator (ICD) system, cardiac resynchronization therapy defibrillator (CRT-D) system, cardioverter system, or combinations thereof. Although medical system 20 is described in the context of sensing electrical activity of and delivering electrical stimulation to the heart of patient 12, the techniques for detecting lead related conditions of this disclosure may be applicable to other medical devices and/or other therapies. In general, the techniques described in this disclosure may be implemented by any medical device, e.g., implantable or external, that includes leads to sense and/or deliver electrical signals to a patient, or any one or more components of a system including such a medical device. As one alternative example, IMD 26 may be a neurostimulator that delivers electrical stimulation to and/or monitor conditions associated with the brain, spinal cord, or neural tissue of patient 16.

In addition, it should be noted that system 20 may not be limited to treatment of a human patient. In alternative examples, system 20 may be implemented in non-human patients, e.g., primates, canines, equines, pigs, and felines. These other animals may undergo clinical or research therapies that may benefit from the subject matter of this disclosure.

The lead bodies of leads 28 and 30 implanted for cardiac applications tend to be continuously flexed by the beating of heart 32. Other stresses may also be applied to the lead bodies, including the stresses from conductors therein rubbing or abrading the lead body (lead-lead interaction, lead-device interaction), during implantation, lead repositioning, or during the flexing caused by the beating of the heart. Patient movement can additionally cause the route traversed by the lead body to be constricted or otherwise altered, causing stresses on the lead bodies and/or conductors. Even without stresses, lead insulation materials or joints may degrade inside the human body. In rare instances, such stresses or degradations may cause a breach in the lead bodies of leads 28 or 30 and possibly externalization of one or more of the conductors of leads 28 or 30.

In some instances, the rubbing and abrading of one or more of the conductors and the lead body within which the one or more conductors are contained may result in not only a breach in the lead body and externalization of the conductor(s), but also a breach or wearing down of the outer insulation of the conductor itself. As such, in some instances, the conductive core of the conductor may be directly exposed to the surrounding bodily fluid upon externalization and/or breach of the non-conductive leady body and outer insulation of the conductor(s). In other instances, the outer insulation of the conductor is not damaged to the point of direct exposure of the conductive core of the conductor(s). In still other embodiments, the outer insulation of the lead body is breached, but the conductor(s) stays within the lead body, i.e., no externalization exists.

Such lead body insulation breaches and/or externalizations can occur anywhere along the lead, including near the proximal end of the lead located adjacent to the housing 34 of IMD 26. The externalization of one or more conductors of leads 28 or 30 may cause lead integrity conditions, such as short circuits or open circuits, that may result in inappropriate sensing (e.g., oversensing and undersensing) and/or therapy operation of IMD 26. For example, IMD 26 may not deliver therapy (such as high voltage defibrillation therapy) when such therapy is desired, may generate stimulation therapy that is not successfully conducted to the heart, or delivery therapy when no such therapy is needed or desired.

Identification of lead related conditions may allow modifications of the stimulation therapy or sensing, or lead replacement. For example, upon identification of a lead related condition, a physician may reprogram the electrodes used for delivering a therapy such that the electrode associated with the conductor affected by the lead-related condition is not utilized. One particular cause of lead related conditions, e.g., the externalization of lead conductors, may be particularly challenging to identify using conventional lead integrity tests, such as impedance monitoring tests. The externalization of conductors may be detected in a clinic, hospital or operating room setting using fluoroscopy/x-ray or defibrillation shock testing, which both have major disadvantages. Fluoroscopy, for example, uses ionizing radiation, which is preferably used as sparingly as possible. To identify these potential externalizations, the patient may need to be subjected to fluoroscopy each visit or even more in instances where the patient is identified as having a lead that is prone to externalizations. Defibrillation shock testing is uncomfortable for the patient and unnecessarily wears down the power source of IMD 26.

This disclosure provides an alternative technique to fluoroscopy and defibrillation shock testing and impedance measurements taken by the device that may be ineffective for identifying insulation breaches and/or externalization of lead conductors. Medical system 20 includes an external signal generator 22 connected to electrodes 50 and 52.

Signal generator 22 may be a handheld computing device or a computer workstation. Signal generator 22 may include a user interface that receives input from a user, such as a clinician, to select the type of test signal to be generated. The user interface may include, for example, a keypad and a display, which may for example, be a cathode ray tube (CRT) display, a liquid crystal display (LCD) or LED display. The keypad may take the form of an alphanumeric keypad or a reduced set of keys associated with particular functions. In some embodiments, a display of signal generator 22 may include a touch screen display, and a user may interact with signal generator 22 via the display.

Electrodes 50 and 52 may be placed in contact with the skin of patient 12. In one example electrodes 50 and 52 may be placed on the skin patient 12 using an adhesive patch, strap, adhesive or other attachment mechanism, or held in place by patient 12, a physician, technician or other individual. Although illustrated as being placed on a chest electrodes 50 and 52 may be placed at other locations on patient 12, including on the hands, shoulders, feet, neck, legs, other location, or combination of locations. In other instances, more than two electrodes may be placed at various locations on patient 12. Such an example is described with respect to FIG. 2. In still further instances, patient 12 may hold onto an apparatus having two handles, each of which functions as one of electrodes 50 and 52. For example, the apparatus may be a cylinder or other shaped apparatus having two electrodes separated by an insulator.

Electrodes 50 and 52 may be placed such that leads 28 and 30 are located between the electrical path between electrodes 50 and 52 such that leads 28 and 30 are subject to the test signal transmitted between electrodes 50 and 52. The orientation of electrodes 50 and 52 with respect to lead 28 and 30 may affect the amount of current induced on the conductors of leads 28 and 30. For example, the signal induced on a sensing vector of leads 28 or 30 is larger when the vector formed between electrodes 50 and 52 is substantially parallel to the vector between the breached conductor and other intact electrode of the sensing electrode pair than when the vector formed between electrodes 50 and 52 is substantially perpendicular to the vector between the breached conductor and other intact electrode of the sensing electrode pair. Thus, in some instances, it may be desirable that the vector between electrodes 50 and 52 be configured such that it is not likely to be substantially perpendicular to the vector between the breached conductor and other intact electrode of the sensing electrode pair. However, external vectors formed by electrodes 50 and 52 that have intermediate angles between the parallel and perpendicular orientations can also be used to deliver the test signals.

A user, such as a physician, technician, or other clinician, or the patient, may interact with signal generator 22 to deliver a test signal or test signals into the body of patient 12 using electrodes 50 and 52. The test signal generated and delivered by signal generator 22 may have any of a number of different morphologies, amplitudes, frequencies, duty cycles, or other characteristics. Signal generator 22 may deliver test signal(s) that includes pulses at a rate not to satisfy an arrhythmia detection algorithm of IMD 26, such as delivery of 1 second bursts every 3 seconds. For example, the test signal may be a sine wave, square wave, triangle wave, sine squared pulse, or other morphology. The test signal may also have an amplitude that is dependent on the pain perception of the patient and possibly below the threshold of perception. It may be desirable that the signal generator 22 is configured to generate the test signal to be within a pass band of any sense amplifier(s) or other components of IMD 26. In some instances, the test signal is a constant current source to avoid the effects of various impedances on the patient skin. Signal generator 22 may, in one example, generate a test signal having a pre-determined amplitude, waveform and frequency. In another example, signal generator 22 may generate a plurality of test signals having different amplitudes, frequencies, and/or waveforms. Signal generator 22 may include a non-transitory computer-readable storage medium having instructions that, when executed, cause a processor of signal generator 22 to provide the functions attributed to test signal generator 22 in the present disclosure.

IMD 26 measures electrical signals on one or more sensing vectors of leads 28 and 30 during delivery of the test signal. A sensing vector may be between any of electrodes 38, 40, 42, 44, 46, and 48 and the housing electrode (sometimes referred to as the "can" electrode). IMD 26 may, for example, measure electrical signals sensed by any of a number of sensing vectors, such as the sensing vectors between tip electrode 38 and ring electrode 42, between defibrillation electrode 46 and defibrillation electrode 48, between tip electrode 38 and defibrillation electrode 46, between ring electrode 32 and defibrillation electrode 46, between tip electrode 38 and defibrillation electrode 48, between ring electrode 42 and defibrillation electrode 48, or between any one of electrodes 38, 42, 46, 48 and the housing or can electrode. In further instances, the sensing vector may be between one of the electrodes on lead 28 or 30 and another electrode on one of the other leads 28 or 30.

In the case of a lead 28 or 30 with an insulation breach and/or externalization, the test signal on at least one of the sensing vectors may result in a signal on one or more conductors of the lead with unique characteristics compared to the signal that would be generated by the test signal on an intact lead (e.g., amplitude difference, change in waveform morphology, or the like). For example, the test signal may generate an electrical signal having a larger amplitude on a lead with an insulation breach/externalization than an electrical signal generated on a lead with no insulation breach or externalization.

IMD 26 may analyze the signals measured on the conductors of leads 28 and 30 during application of the test signal(s) by signal generator 22 to determine whether a lead related condition exists, such as a lead body insulation breach or externalization of one or more lead conductors. As described above, an electrical signal induced on leads 28 or 30 by the test signal may have a larger amplitude when a lead related condition such as a breach in the insulation of the lead body or externalization of one or more of the conductors is present. IMD 26 may compare an amplitude of the electrical signals sensed by the various sensing vectors to a threshold amplitude and detect an insulation breach and/or externalization of a lead conductor when the amplitude of the electrical signal sensed during the delivery of the test signal is greater than the threshold. The threshold may be determined based on the amplitude of a test signal expected to be generated on an intact lead, i.e., a lead with no lead-related condition. The threshold may be computed by the manufacturer for a type of lead or may be determined upon implantation by applying test signal and measuring the amplitude of the induced signals on a particular lead. In other instances, IMD 26 may compare a characteristic of the electrical signal measured on leads 28 or 30 in addition to or instead of the amplitude to determine whether a lead related condition is present. The other characteristics analyzed may include, for example, a waveform morphology, frequency, phase, slope, polarity, or other characteristic.

Although described in the context of providing the test signal to patient 12 using electrodes 50 and 52 in contact with the skin of patient 12, the techniques of this disclosure should not be so limited. Signal generator 22 may, for example, include one or more probes having one or both of electrodes 50 or 52 that are inserted within patient 12. Alternatively, signal generator 22 may generate a wireless test signal, e.g., a radio frequency (RF) test signal. Moreover, in further instances, IMD 26 may deliver the test signal to patient 12 using one or more of electrodes 38, 40, 42, 44, 46, and 48 and/or the housing electrode. For example, IMD 26 may deliver a test signal via an electrode pair and measure a signal on one or more sensing vectors. In the examples in which IMD 26 delivers the test signal to patient 12, system 20 would not include signal generator 22 or electrodes 50 and 52.

Medical system 20 may also include a programmer 24 that communicates with IMD 26. IMD 26 and programmer 24 may communicate using any of a variety of wireless communication techniques known in the art. Examples of communication techniques may include, for example, low frequency inductive telemetry or RF telemetry, although other techniques are also contemplated. Programmer 24 may be a handheld computing device, desktop computing device, a networked computing device, or other computing device configured to communicate with IMD 26. Programmer 24 may include a non-transitory computer-readable storage medium having instructions that, when executed, cause a processor of programmer 24 to provide the functions attributed to programmer 24 in the present disclosure.

Programmer 24 transmits and receives data from IMD 26. In accordance with one aspect of this disclosure, programmer 25 may be configured to transmit a communication to IMD 26 to notify IMD 26 of the upcoming lead integrity test, e.g., the subsequently delivered test signals from signal generator 22. IMD 26 may, in response to the communication from IMD 26, alter operation of IMD 26 such that any signal sensed on leads 28 or 30 is not processed as sensed cardiac events. For example, IMD 26 may disable detection or high voltage therapy functionality during the lead integrity testing described herein. Alternatively or additionally, IMD 26 may alter operation to ensure that any signal sensed on lead 28 or 30 is not filtered out. IMD 26 may, for instance, adjust settings of IMD 26 to increase a dynamic range of one or more sensing components (e.g., filters) of IMD 26.

Programmer 24 may also retrieve data from IMD 26, including cardiac EGMs stored by IMD 26 during the lead integrity testing described herein. In this manner, the EGM signals measured during delivery of the test signals by signal generator 22 or IMD 26 may be analyzed by programmer 24 to identify whether the test signal on leads 28 or 30 is indicative of a lead condition, such as insulation breach or externalization of a lead conductor. Analyzing the cardiac EGMs during the lead integrity testing using programmer 24 may be particularly advantageous in performing lead integrity testing on legacy devices, e.g., devices that are already implanted and do not include the algorithms necessary for detecting the lead-related conditions. In some instances, the programmer may simply display the EGMs or other signals measured by IMD 26 during delivery of the test signals and the physician or other personnel may analyze the EGMS to detect the lead-related conditions. Other external devices besides programmer 24 may analyze the EGM signals measured during delivery of the test signals to identify whether the signal on leads 28 or 30 is indicative of a lead condition, such as an external server (e.g., Medtronic CareLink®).

In the instances in which IMD 26 analyzes the EGM signal measured during delivery of the test signals by signal generator 22 or IMD 26 to identify whether the test signal on leads 28 or 30 is indicative of a lead related condition, such as insulation breach or externalization of a lead conductor, IMD 26 may transmit an alert or other communication to programmer 24 to indicate whether or not lead condition is detected.

Data retrieved by programmer 24 may also include additional information regarding the performance or integrity of IMD 26 or other components of medical system 20, such as leads 28 and 30, or a power source of IMD 26. In some examples, this information may be presented to the user as an alert. For example, IMD 26 may also transmit other information related to lead integrity checks, such as any abnormal impedance measurements detected. In this manner, programmer 24 may analyze data related to the lead integrity analysis described herein with other lead integrity checks, such as impedance checks that may identify other lead related conditions including fractured conductors, shorts between conductors and the like. Programmer 24 may present a comprehensive lead integrity report to the user based on the analysis.

Programmer 24 may also transfer data to IMD 26. Data transferred to IMD 26 using programmer 24 may include, for example, values for operational parameters, electrode selections used to deliver electrical stimulation, waveform selections used for electrical stimulation, configuration parameters for detection algorithms, or other data. In some instances, signal generator 22 may be incorporated within programmer 24 such that the two components comprise a single external device. In other words, a single external device may communicate with IMD 26 and provide the test signal for identifying insulation breach and/or externalization of one or more lead conductor(s).

Figure 2:
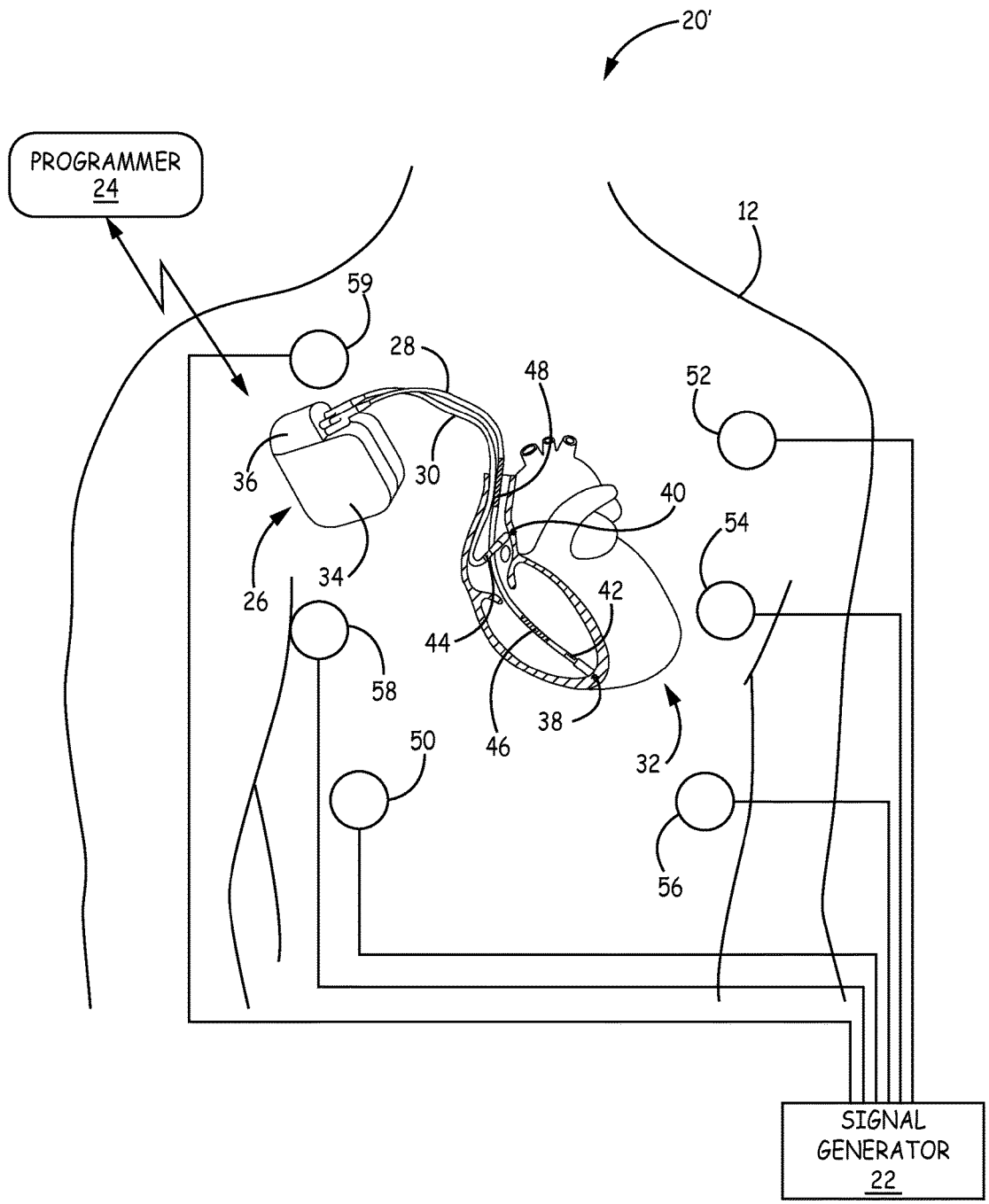
FIG. 2 is a conceptual diagram of another example medical system.

FIG. 2 is a conceptual diagram of another example medical system 20'. Medical system 20' substantially conforms to medical system 20 of FIG. 1 except an array of electrodes are placed on patient 12 instead of a pair of electrodes 50 and 52. In particular, in addition to electrodes 50 and 52, system 20' includes electrodes 54, 56, 58, and 59 attached to or otherwise contacting the body of patient 12. In some instances, the array of electrodes may be included within a vest, belt, or other article that could be positioned around the chest of patient 12.

As described above with respect to FIG. 1, the orientation of electrodes 50 and 52 with respect to lead 28 and 30 may affect the amount of current induced on the conductors of leads 28 and 30. For example, the signal induced on a sensing vector of leads 28 or 30 is larger when the vector formed between the external electrodes delivering the test signal is substantially parallel to the vector between the breached conductor and other intact electrode of the sensing electrode pair than when the external electrode vector is substantially perpendicular to the sensing vector of the sensing electrode pair. By providing a plurality of electrodes 50, 52, 54, 56, 58, and 59 the physician or other individual may select various electrode vectors for use in delivering the test signal from signal generator 22 to increase the likelihood that one of the external electrode vectors used to deliver the test signal is oriented in a manner to generate signals on the conductors of lead 28 or 30 that, when a breach or externalization exists, have an amplitude or other characteristic that is identifiably different than the signal generated or expected to be generated on the intact lead.

In some instances, signal generator 22 may be configured to generate a plurality of test signals and consecutively deliver subsequent test signals via different pairs of electrodes 50, 52, 54, 56, 58, and 59. For example, signal generator 22 may deliver a first test signal using electrodes 50 and 52, a second test signal using electrodes 54 and 59, and a third test signal using electrodes 56 and 58. The example is for illustrative purposes only. Signal generator 22 may deliver test signals via any number of combinations of electrodes 50, 52, 54, 56, 58, and 59. Moreover, system 20' may include more or fewer external electrodes attached to or otherwise contacting patient 12.

Delivering the test signals using different pairs of electrodes 50, 52, 54, 56, 58, and 59 increases the likelihood that one of the vectors used to deliver the test signals is oriented with respect to the major length of leads 28 or 30 to generate signals on the conductors of lead 28 or 30 that have substantial differences in amplitude or other characteristic compared to an intact lead. In the instances in which signal generator 22 generates a plurality of test signals, IMD 26 may analyze each of the signals and detect a lead-related condition when any one of the signals generated on leads 28 or 30 has an amplitude (or other characteristic) that exceeds (or otherwise differs from) the respective threshold.

Figure 3:
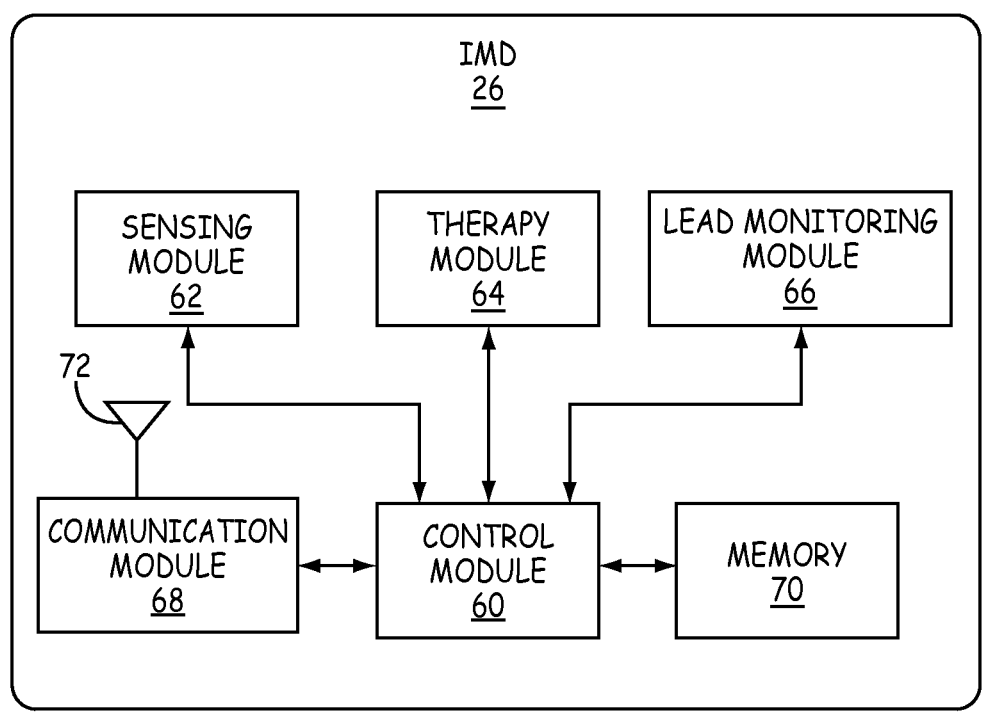
FIG. 3 is a functional block diagram of an example configuration of electronic components of IMD.

FIG. 3 is a functional block diagram of an example configuration of electronic components of IMD 26. IMD 26 includes a control module 60, sensing module 62, therapy module 64, lead monitoring module 66, communication module 68, and memory 70. The electronic components may receive power from a power source (not shown in FIG. 3), which may be a rechargeable or non-rechargeable battery. In other embodiments, IMD 26 may include more or fewer electronic components. The described modules may be implemented together on a common hardware component or separately as discrete but interoperable hardware or software components. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

Therapy module 64 is configured to generate and deliver electrical stimulation therapy to heart 32. Therapy module 64 may include one or more pulse generators, capacitors, and/or other components capable of generating and/or storing energy to deliver as pacing therapy, defibrillation therapy, cardioversion therapy, cardiac resynchronization therapy, other therapy or a combination of therapies. Control module 60 may control therapy module 64 to generate electrical stimulation therapy and deliver the generated therapy to heart 32 via one or more combinations of electrodes 38, 40, 42, 44, 46, and 48 and an indifferent housing electrode according to one or more therapy programs, which may be stored in memory 70. Control module 60 controls therapy module 64 to generate electrical stimulation therapy with the amplitudes, pulse widths, timing, frequencies, electrode combinations or electrode configurations specified by a selected therapy program.

Therapy module 64 may deliver electrical stimulation therapy via any of a number of pairs of electrodes 38, 40, 42, 44, 46, and 48 and the indifferent housing electrode. For defibrillation therapy for example, one or more defibrillation shocks may be delivered to heart 32 via one or both defibrillation electrodes and/or the housing electrode. As another example, pacing therapies may be delivered via a bipolar electrode configuration using pairs of tip and ring electrodes, such as tip and ring electrodes 38 and 42 of lead 28 or tip and ring electrodes 40 and 44 of lead 30 or via a unipolar electrode configuration, e.g., using electrodes 38 and 40 in combination with a housing electrode of IMD 26. Therapy module 64 may include a switch module (not shown) that control module 60 may configure to select which of the available electrodes are used to deliver the stimulation therapy.

Sensing module 62 is electrically coupled to some or all of electrodes 38, 40, 42, 44, 46, and 48 via the conductors of leads 28 and 30 and one or more electrical feedthroughs, or to the housing electrode via conductors internal to housing 26. Sensing module 62 is configured to obtain signals sensed via one or more combinations of electrodes 38, 40, 42, 44, 46, and 48 and the housing electrode and process the obtained signals. The components of sensing module 62 may be analog components, digital components or a combination thereof Sensing module 62 may, for example, include one or more sense amplifiers, filters, rectifiers, threshold detectors, analog-to-digital converters (ADCs) or the like. Sensing module 62 may convert the sensed signals to digital form and provide the digital signals to control module 60 for processing or analysis. For example, sensing module 62 may amplify signals from the sensing electrodes and convert the amplified signals to multi-bit digital signals by an ADC. Sensing module 62 may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to control module 60.

Sensing module 62, like therapy module 64, may include a switch module (not shown) that control module 60 may configure to select which of the available electrodes are used to sense electrical signals. The switch module may be a common switch module that is shared with therapy module 64 or a separate switch module. In some instances, switch module may allow more than one sensing vector (e.g., pair of electrodes) to sense signals concurrently.

Control module 60 may process the signals from sensing module 62 to monitor electrical activity of heart 32 of patient 12. Control module 60 may store signals obtained by sensing module 62 as well as any generated EGM waveforms, marker channel data or other data derived based on the sensed signals in memory 70. Control module 60 may analyze the EGM waveforms and/or marker channel data to detect cardiac events (e.g., tachyarrhythmias). In response to detecting the cardiac event, control module 60 may control therapy module 64 to deliver the desired therapy to treat the cardiac event.

As described above with respect to FIG. 1, in rare instances lead bodies of leads 28 and 30 implanted for cardiac applications may become damaged over time due to stresses caused by continuous flexing, rubbing between two lead bodies, rubbing between one lead body and housing 34, patient movement, material degradation or the like. The damage to the lead bodies may, for example, include a breach in the insulation of the lead body and possibly externalization of one or more of the conductors of leads 28 or 30. In addition, the insulation of the conductors themselves may be damaged or worn down such that the conductive core of the conductor may be directly exposed to the surrounding bodily fluid upon externalization and/or breach of the insulating lead body and outer insulation of the conductor(s). Such lead body insulation breaches and/or externalizations can result in inappropriate operation of IMD 26. For example, IMD 26 may not deliver therapy (such as high voltage defibrillation therapy) when such therapy is desired, may generate stimulation therapy that is not successfully conducted to the heart, or deliver therapy when no such therapy is needed or desired.

IMD 26 includes a lead monitoring module 66 that monitors for lead related conditions, including the insulation breaches and externalizations described above. Lead monitoring module 66 may analyze one or more criteria to determine if a lead-related condition exists. Lead monitoring module 66 may, for example, analyze impedance values associated with leads 28 and 30 to determine whether a lead-related condition exists. As described herein, however, certain causes of lead related conditions, e.g., breach in lead body or the externalization of lead conductors, may be particularly challenging to identify using the impedance monitoring tests.

Lead monitoring module 66 may therefore analyze signals induced on the conductors of the lead by a known signal source and determine whether a lead-related condition (such as a breach and/or externalization) exists. In one example, the signal source may be an external signal generator 22 connected to leads 60 and 62 attached to the body of patient 12. In another example, the signal source may be signals generated by IMD 26 itself.

During delivery of the test signal (whether externally generated or generated by IMD 26), lead monitoring module 66 measures electrical signals on one or more sensing vectors of leads 28 and 30 and analyzes one or more characteristics of the measured signals to determine if a lead-related condition exists. For a lead having an insulation breach and/or externalization, the signal measured on the lead during delivery of the test signal has characteristics different than an intact lead. For example, the electrical signal induced on the lead by the test signal may have a larger amplitude when a lead related condition such as a breach in the insulation of the lead body or externalization of one or more of the conductors is present. Lead monitoring module 66 may therefore compare an amplitude of the electrical signals sensed by the various sensing vectors to a threshold amplitude and detect an insulation breach and/or externalization of a lead conductor when the amplitude of the electrical signal sensed during the delivery of the test signal is greater than the threshold amplitude. In some instances, the threshold amplitude may be a particular percentage larger than the expected amplitude. This percentage may vary based on the amplitude of the test signal, the orientation of the electrode vector delivering to the test signal or the like. In one example, the threshold amplitude may range from approximately 10% to approximately 50% depending on the various parameters. In other instances, the threshold amplitude may be determined based on the amplitude of the test signal.

In other instances, lead monitoring module 66 may compare other characteristics of the electrical signal measured on leads 28 or 30 in addition to or instead of the amplitude to determine whether a lead related condition is present. The other characteristics analyzed may include, for example, a waveform morphology, phase, slope, polarity, frequency spectral component of the QRS complex, or other characteristic or combination of characteristics.

As described with respect to FIG. 2, signal generator 22 may deliver a plurality of test signals using different pairs of external electrodes. In this case, IMD 26 may analyze the signals generated on the conductors of leads 28 or 30 and detect a lead-related condition when any one of the signals meets the lead-related condition criteria.

In response to lead monitoring module 66 detecting a lead-related condition, control module 60 may adjust one or more settings of IMD 26. Control module 60 may adjust an electrode vector used for delivering therapy to heart 32 and/or sensing electrical signals from heart 32. For example, control module 60 may adjust the electrode vector used for delivering defibrillation therapy such that the conductor having the breach and/or externalization is not used for delivery of the defibrillation therapy. If the electrode vector for delivery of defibrillation therapy included defibrillation electrode 46, control module 60 may configure the electrode vector to not include defibrillation electrode 46, but instead utilize defibrillation electrode 44 and the housing electrode to deliver defibrillation therapy.

Additionally, control module 60 may cause IMD 26 to generate an alert to notify patient 12 and/or a physician or other person that a lead-related condition has been detected. IMD 26 may transmit the alert via communication module 68. Communication module 68 includes any suitable hardware, firmware, software or any combination thereof for communicating with another device, such as programmer 24, signal generator 22, a patient monitoring device. For example, communication module 68 may include appropriate modulation, demodulation, frequency conversion, filtering, and amplifier components for transmission and reception of data with the aid of antenna 72. Antenna 72 may be located within connector block 36 of IMD 26 or within housing 34 of IMD 26. In one example, antenna 72 may be an inductive coil antenna within housing 34 of IMD 26. In another example, antenna 72 may be an RF antenna located within connector block 36 and coupled to communication module 68 via a feedthrough. In a further example, IMD 26 may include both an inductive coil antenna and an RF antenna coupled to communication module 68 or other antenna located within or outside of housing 34.

In embodiments in which IMD 26 generates and delivers the test signals, lead monitoring module 66 may include the components necessary to inject an test signal. For example, lead monitoring module 66 may include a signal generator that generates the test signal. In some instances, the signal generator may be used for generating the test signals as well as for other purposes, e.g., for generating signals for lead impedance measurements, for generating electrical stimulation therapy, for generating signals for telemetry communications, or the like. In this case, IMD 26 would not need additional circuitry.

The various modules of IMD 26 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Memory 70 may include computer-readable instructions that, when executed by control module 60 or other component of IMD 26, cause one or more components of IMD 26 to perform various functions attributed to those components in this disclosure. Memory 70 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

Figure 4:
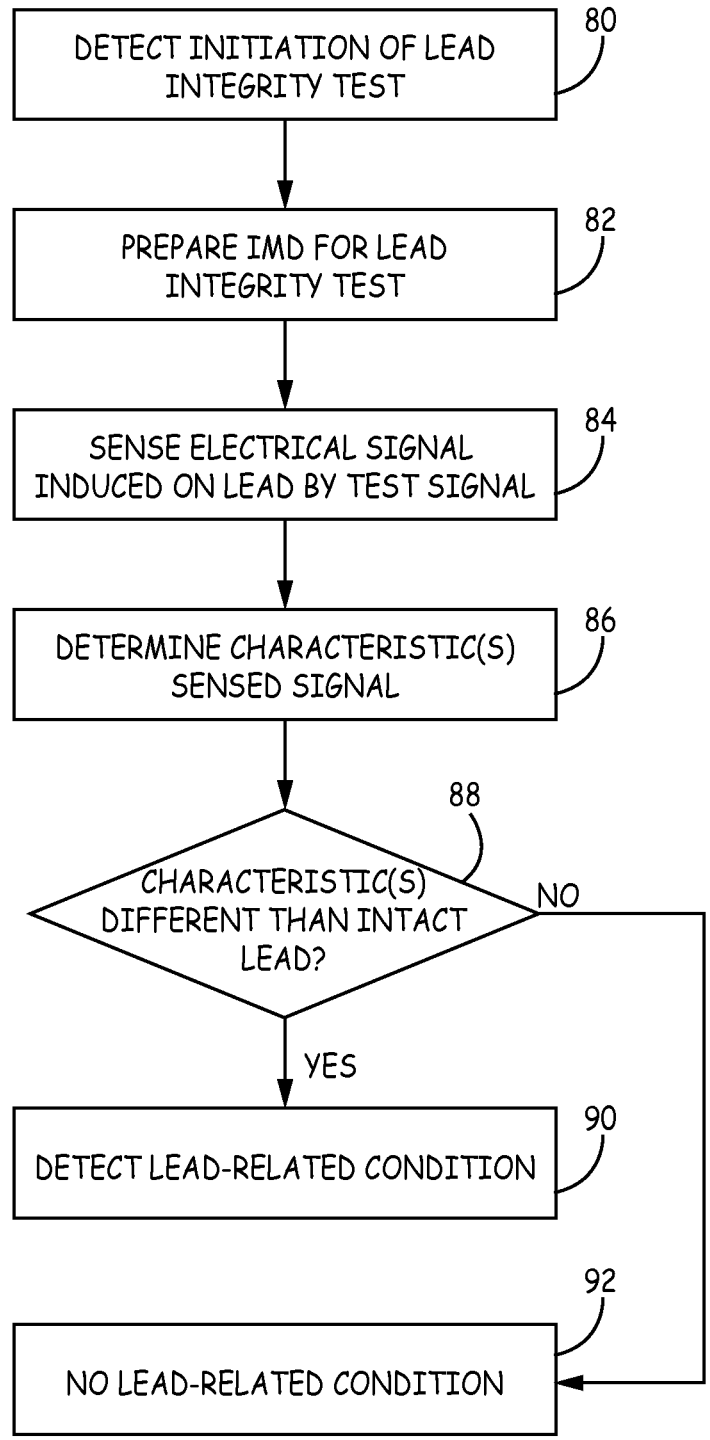
FIG. 4 is a flow diagram illustrating example operation of an IMD operating in accordance with the techniques of this disclosure to analyze signals to detect a lead-related condition.

FIG. 4 is a flow diagram illustrating example operation of an IMD, such as IMD 26, operating in accordance with the techniques of this disclosure. Initially, IMD 26 detects initiation of lead integrity testing (80). In instances in which the test signal is generated from an external device, communication module 58 of IMD 26 may receive a communication from signal generator 22 or programmer 24 to alert IMD 26 of initiation of the lead integrity testing. The lead integrity testing may be performed periodically, e.g., at each follow-up visit. In instances in which the signal is generated by IMD 26, control module 50 may receive an indication from lead monitoring module 56 or an interrupt signal from control module 50. IMD 26 may periodically perform the lead integrity testing, e.g., daily, weekly, monthly or at other time intervals. Alternatively, or additionally, IMD 26 may perform the lead integrity testing upon another condition being met, e.g., impedance measurements being out of range or other indicator or lead failure being present.

Control module 50 of IMD 26 may prepare IMD 26 to sense for the signals induced on the lead conductors by the test signals generated by signal generator 22 (82). For example, IMD 26 may select a particular sense vector on which to sense for the signals generated by the test signal. In another example, control module 58 may adjust one or more settings of sensing module 52 to increase a dynamic range of one or more sensing components (e.g., filters) of IMD 26.

IMD 26 senses an electrical signal generated on one or more sensing vectors of the lead by the test signal (84). IMD 26 determines one or more characteristics of the sensed electrical signal (86). In one example, sensing module 52 and/or control module 50 may determine an amplitude of the sensed signal. The amplitude may be measured at a particular point in the cardiac cycle, such as during diastasis. Diastasis is the middle stage of diastole during the cycle of a heartbeat, where the initial passive filling of the heart's ventricles has slowed down, but before the atria contract to complete the filling. Because there is typically no electrical activity of heart 32, the signals associated with electrical activity of the heart will not be mistaken for test signals sensed on the sensing vector. In other instances, sensing module 52 and/or control module 50 may determine a waveform morphology of the sensed signal or other characteristic of the sensed signal. Control module 50 determines whether the characteristic(s) of the sensed signal is different than the expected characteristic of a signal generated on an intact lead (88). For example, control module 50 may compare the determined amplitude of the sensed electrical signal to a threshold amplitude. The expected characteristics may be determined based on testing performed on an intact lead after implantation (possibly allowing for a period of stabilization). For example, a baseline signal may be sensed using the test signal and a relative threshold may be determined based on the baseline signal.

When control module 50 determines that the characteristic(s) of the sensed signal is different than the expected characteristic of a signal generated on an intact lead (e.g., an amplitude of the sensed electrical signal is greater than a threshold amplitude), control module 50 detects a lead-related condition on the lead (90). When control module 50 determines that the characteristic(s) of the sensed signal is not different than the expected characteristic of a signal generated on an intact lead (e.g., an amplitude of the sensed electrical signal is not greater than a threshold amplitude), control module 50 does not detect a lead-related condition on the lead (92).

The assessment of the lead to detect a lead-related condition described in FIG. 4 may be performed on more than one sensing vector of the lead. In one example, IMD 26 may consecutively assess different sensing vectors using the techniques described. For instance, IMD 26 may sense and analyze signals on a first sensing vector of lead 28, sense and analyze signals on a second sensing vector of lead 28, and so on. This may be done for a subset of sensing vectors or for all possible sensing vectors. In another example, IMD 26 may concurrently sense electrical signals and assess the electrical signals for multiple sensing vectors simultaneously.

Moreover, the assessment may include sensing and analyzing more than one electrical signal corresponding with more than one test signal. For example, an external device may deliver a plurality of test signals using different pairs of electrodes to ensure that at least one of the test signals generates an electrical signal on a breached or externalized lead conductor that is sufficiently different from what is expected on an intact lead. In this case, a lead-related condition may be detected when any one of the test signals generates a signal on a sensing vector that is sufficiently different from the electrical signal expected on an intact lead.

Although each of the steps described in FIG. 4 are described as occurring within IMD 26, one or more of the steps may be performed in another device, such as in a programmer device 22, a patient monitoring device (e.g., remote patient monitoring device or handheld patient monitoring device) or other device. For example, IMD 26 may transmit the sensed signals to the other device, which may then process those signals to assess whether or not a lead related condition exists.

Figure 5:
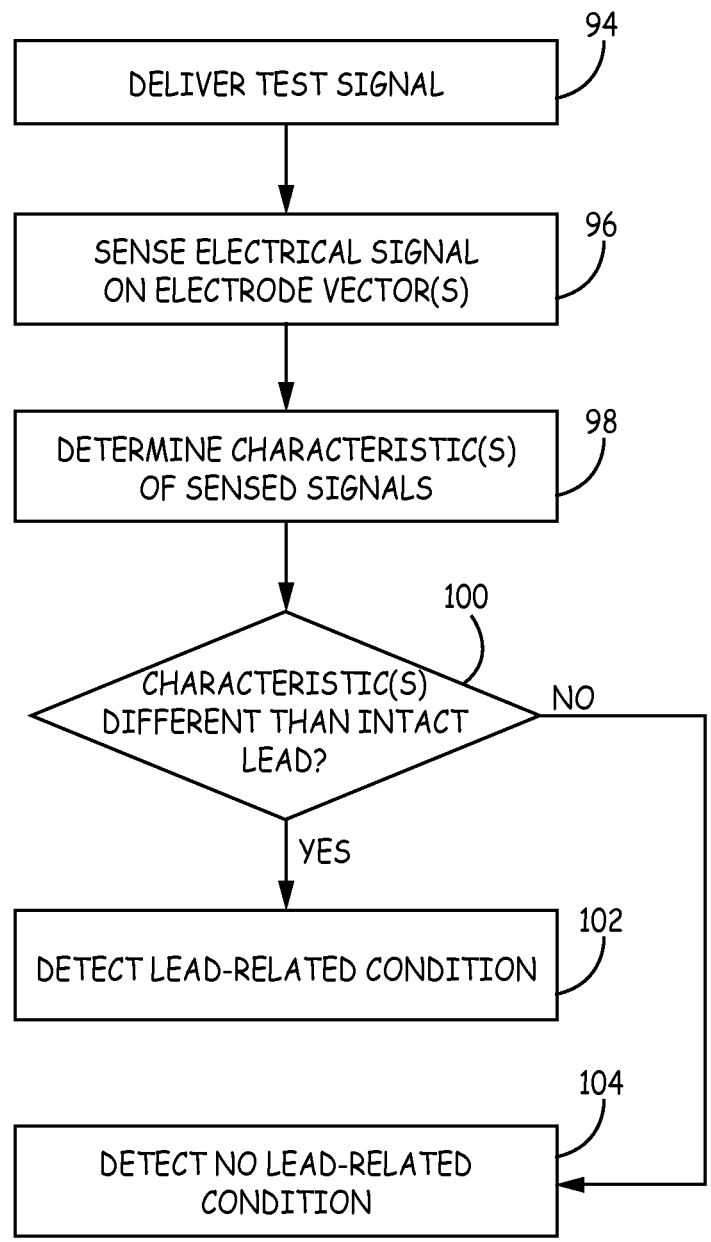
FIG. 5 is a flow diagram illustrating example operation of an IMD performing a lead integrity check on a lead in accordance with one aspect the techniques of this disclosure.

FIG. 5 is a flow diagram illustrating example operation of an IMD performing a lead integrity check on a lead in accordance with one aspect the techniques of this disclosure. For purposes of example, FIG. 5 will be described in the context of IMD 26 performing the lead integrity check of lead 28. IMD 26 may periodically perform the lead integrity testing, e.g., daily, weekly, monthly or at other time intervals. Alternatively, or additionally, IMD 26 may perform the lead integrity testing upon another condition being met, e.g., impedance measurements being out of range or other indicator or lead failure being present. IMD 26 may deliver a test signal via a pair of electrodes (94). The pair of electrodes may be both located on lead 28 or one electrode may be located on lead 28 and the other electrode of the pair may be the housing (or can) electrode or even include electrodes of another lead, such as lead 30. For example, IMD 26 may deliver the test signal using tip electrode 38 and the housing electrode. In another example, the test signal may be delivered between defibrillation electrodes 46 and 48. The test signal may be a low amplitude pulse, such as subthreshold pacing pulse or series of pulses. In some instances, the signal may be a sine or squared signal or multiple signals delivered with different characteristics, such as different amplitudes, frequencies, pulse widths or the like.

IMD 26 senses electrical signals generated on one or more sensing vectors of the lead by the test signal (96). The sensing vectors will typically be sensing vectors different than the vector used to deliver the test signal. In the example in which the test signal is delivered between tip electrode 38 and the housing electrode, IMD 26 may sense electrical signals generated on the sensing vector formed by ring electrode 42 and defibrillation electrode 46 and sense electrical signals generated on the sensing vector formed by ring electrode 42 and defibrillation electrode 48. In the example in which the test signal is delivered between defibrillation electrodes 46 and 48, IMD 26 may sense electrical signals generated on the sensing vector formed by tip electrode 38 and ring electrode 42 and sense electrical signals generated on the sensing vector formed by tip electrode 42 and defibrillation electrode 46.

IMD 26 determines one or more characteristics of the sensed electrical signals (98). In one example, sensing module 52 and/or control module 50 may determine the amplitude of the sensed electrical signals, a waveform morphology of the sensed electrical signals, or other characteristic of the sensed electrical signals. Control module 50 determines whether the characteristic(s) of the sensed signal is different than the expected characteristic of a signal generated on the sensing vectors of an intact lead (100). For example, control module 50 may compare the determined amplitude of the sensed electrical signal to a threshold amplitude associated with each of the sensing vectors on which the electrical signals were sensed.

When control module 50 determines that the characteristic(s) of the sensed signal is different than the expected characteristic of a signal generated on an intact lead (e.g., an amplitude of the sensed electrical signal is greater than a threshold amplitude), control module 50 detects a lead-related condition on the lead (102). When control module 50 determines that the characteristic(s) of the sensed signal is not different than the expected characteristic of a signal generated on an intact lead (e.g., an amplitude of the sensed electrical signal is not greater than a threshold amplitude), control module 50 does not detect a lead-related condition on the lead (104).

Figure 6:
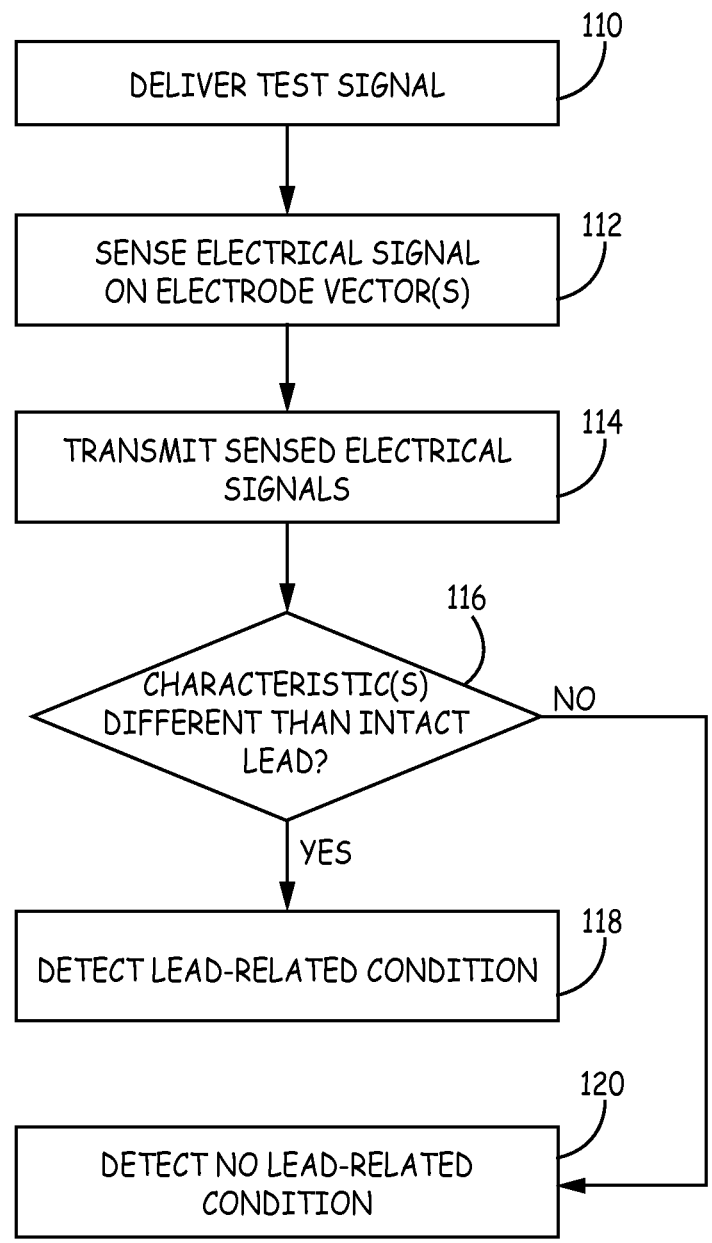
FIG. 6 is a flow diagram illustrating another example process for performing a lead integrity check on a lead in accordance with one aspect of this disclosure.

FIG. 6 is a flow diagram illustrating another example process for performing a lead integrity check on a lead in accordance with one aspect the techniques of this disclosure. Initially, a signal generator delivers one or more test signals via a pair of electrodes (110). The signal generator may be an external signal generator (such as signal generator 22) or may be a signal generator within IMD 26.

IMD 26 senses one or more electrical signals generated on one or more sensing vectors of lead 28 or 30 by the test signal (112). IMD 26 transmits the sensed electrical signals to an external device, such as programming device 24 (114). In other instances, the IMD 26 may transmit the sensed signals to an external device and the sensed signals may be sent to a remote server via one or more networks.

The characteristics of the sensed electrical signals are analyzed to determine whether the characteristic(s) are different than the expected characteristic of a signal generated on the sensing vectors of an intact lead (116). In one example, programming device 24 may include a processor that analyzes the characteristics to determine whether the characteristic(s) are different than the expected characteristic of a signal generated on the sensing vectors of an intact lead. In another example, the programming device 24 may send the sensed electrical signals to a remote server for analysis. In still other examples, programming device 24 and/or remote device may display the sensed electrical signals on a monitor or other display for analysis by a physician.

When it is determined that the characteristic(s) of the sensed signal is different than the expected characteristic of a signal generated on an intact lead (e.g., an amplitude of the sensed electrical signal is greater than a threshold amplitude), a lead-related condition is detected on the lead (118). When it is determined that that the characteristic(s) of the sensed signal is not different than the expected characteristic of a signal generated on an intact lead (e.g., an amplitude of the sensed electrical signal is not greater than a threshold amplitude), a lead-related condition is not detected on the lead (120).

Figure 7A:
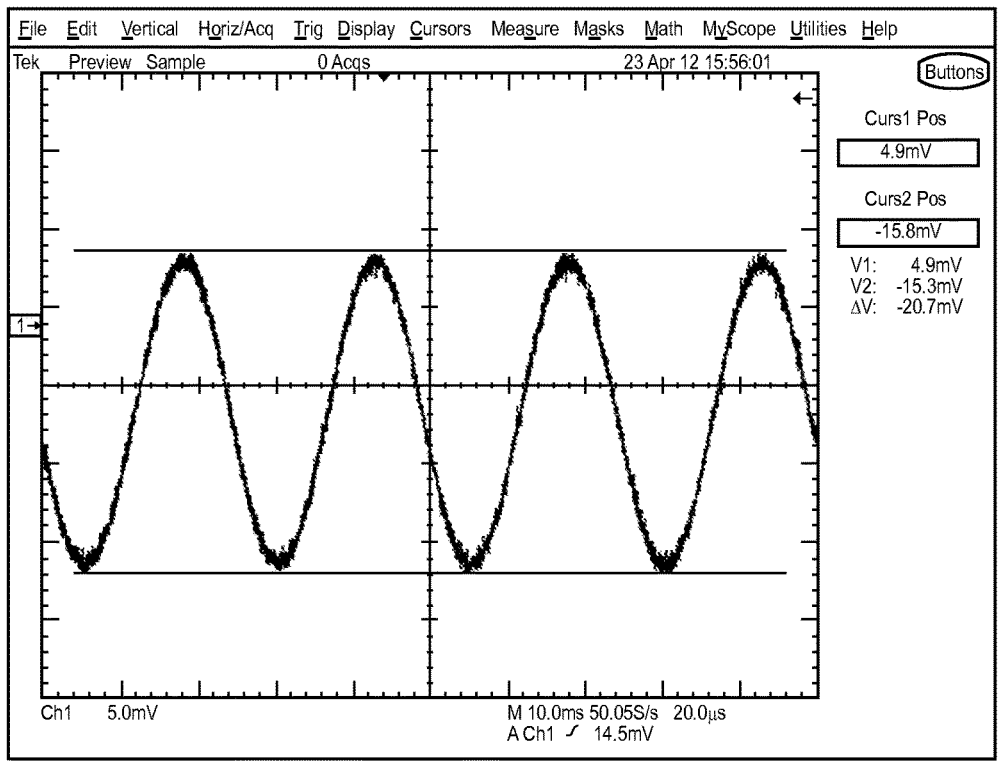
FIG. 7A illustrates an example oscilloscope trace of an electrical signal generated by a test signal on a lead having no insulation breach.
Figure 7B:
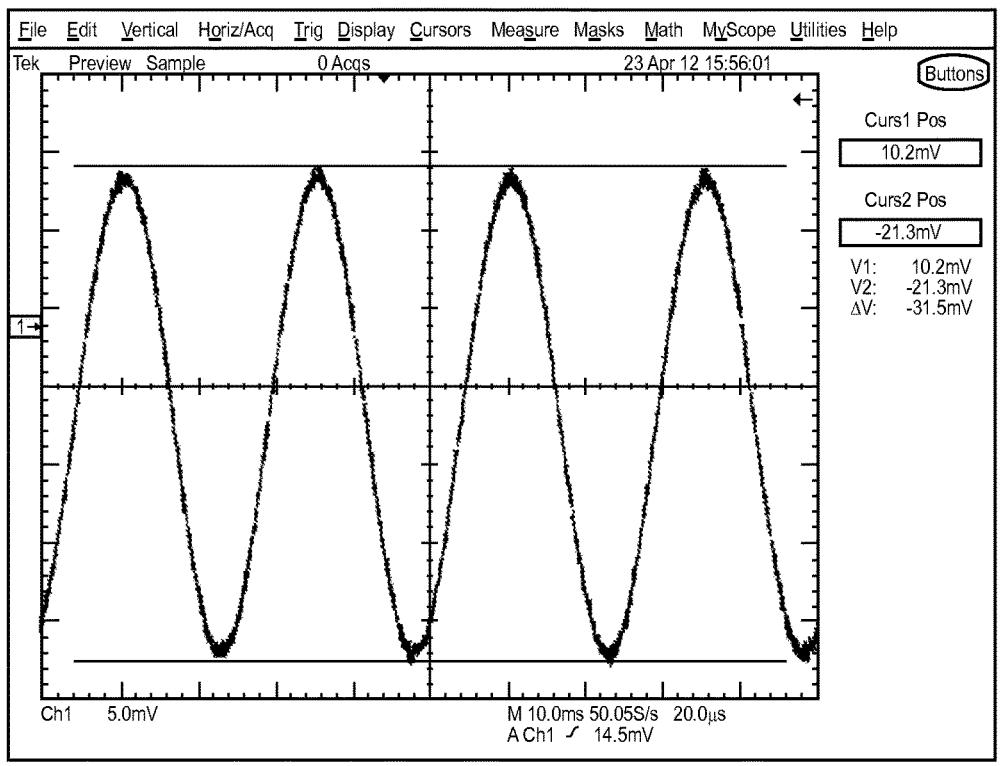
FIG. 7B illustrates an example oscilloscope trace of an electrical signal generated by a test signal on a lead having an insulation breach.

FIGS. 7A and 7B illustrate example oscilloscope traces of an electrical signal generated on leads by a test signal. Two leads were submerged into a tank of saline and a test signal was injected into the tank. One of the leads had no insulation breach while the other lead was modified such that an insulation breach was present. A 9-volt, 40-Hz sinusoid wave was injected into the saline tank and the oscilloscope measure the electrical signals on the submerged leads. The signal measured on the lead having no insulation breach is illustrated in FIG. 7A and the signal measured on the lead having the insulation breach is illustrated in FIG. 7B. As illustrated by the two measured signals, the amplitude of the electrical signal on the lead having the insulation breach is much larger (31.5 mV) than the amplitude of the electrical signal on the lead without an insulation breach (20.7 mV).

Various examples have been described. These and other examples are within the scope of the following claims.

The invention claimed is:

1. A medical device system comprising:
an external system comprising:
at least two electrodes configured to contact a body of a patient; and
a signal generator electrically coupled to the at least two electrodes, the signal generator configured to generate a first electrical signal to be delivered by the at least two electrodes;
an implantable medical system comprising:
an implantable medical device; and
at least one implantable medical lead coupled to the implantable medical device,
wherein the implantable medical system senses a second electrical signal induced on the at least one implantable medical lead by the first electrical signal generated by the signal generator; and
a processor configured to:
identify a characteristic of the second electrical signal that is indicative of at least one of a breach of outer insulation of a lead body of the at least one implantable medical lead or an externalization of a conductor of the at least one implantable medical lead; and
identify the at least one of a breach of the outer insulation of the lead body or an externalization of the conductor based on the identification of the characteristic of the second electrical signal.

2. The system of claim 1, wherein the processor is configured to:
identify the characteristic of the second electrical signal by at least comparing the characteristic of the second electrical signal sensed on the at least one implantable medical lead to a threshold; and
identify the at least one of a breach of the outer insulation of the lead body or an externalization of the conductor based on the comparison.

3. The system of claim 2, wherein the processor is configured to:
identify the characteristic of the second electrical signal by at least comparing an amplitude of the second electrical signal sensed on the at least one implantable medical lead to a threshold amplitude; and
identify the at least one of a breach of the outer insulation of the lead body or an externalization of the conductor when the amplitude of the second electrical signal sensed on the at least one implantable medical lead is greater than the threshold amplitude.

4. The system of claim 3, wherein the threshold amplitude corresponds with an expected amplitude of the second electrical signal induced on the implantable medical lead by the first electrical signal when the implantable medical lead does not have the at least one of a breach of the outer insulation of the lead body or an externalization of the conductor.

5. The system of claim 1, wherein the characteristic of the second electrical signal sensed on the at least one implantable medical lead comprises at least one of an amplitude, a waveform morphology, a frequency, a phase, a slope, and a polarity.

6. The system of claim 1, wherein the processor resides within the implantable medical device.

7. The system of claim 1, wherein the processor resides within an external device.

8. The system of claim 6, wherein the processor resides within one of a patient monitoring device, a programming device, and a remote server.

9. The system of claim 1, wherein processor is configured to adjust a therapy delivered by the implantable medical device in response to identifying the at least one of a breach of the outer insulation of the lead body or an externalization of the conductor.

10. The system of claim 1, wherein the processor is configured to provide an alert to in response to identifying the at least one of a breach of the outer insulation of the lead body or an externalization of the conductor.

11. The system of claim 1, wherein the at least two electrodes comprise patch electrodes that are configured to be placed on the body of the patient.

12. The system of claim 1, wherein the at least two electrodes are configured to contact the body of the patient such that a vector between the at least two electrodes in contact with the body of the patient is not substantially perpendicular to a vector between an externalized conductor of the at least one implantable medical lead and an intact electrode of a sensing electrode pair.

13. The system of claim 1, further comprising:
a control module configured to switch from a first electrode vector used for delivering therapy to a heart of the patient via the at least one implantable lead to a second electrode vector used for delivering therapy to the heart of the patient via the at least one implantable lead in response to the identification of the at least one of a breach of the outer insulation of the lead body or an externalization of the conductor.

14. The system of claim 1, further comprising:
a control module configured to switch from a first electrode vector used for sensing electrical signals from a heart of the patient via the at least one implantable lead to a second electrode vector sensing electrical signals from the heart of the patient via the at least one implantable lead in response to the identification of the at least one of a breach of the outer insulation of the lead body or an externalization of the conductor.

15. The system of claim 1, wherein the processor is configured to:
identify the characteristic of the second electrical signal that is indicative of an externalization of the conductor of the at least one implantable medical lead; and
identify the externalization of the conductor based on the identification of the characteristic of the second electrical signal.

16. A method comprising:
providing a first electrical signal generated by an external signal generator to a body of a patient via a pair of electrodes in contact with the body of the patient;
sensing a second electrical signal induced on at least one implantable medical lead by the first electrical signal generated by the signal generator;
identifying a characteristic of the second electrical signal that is indicative of at least one of a breach of outer insulation of a lead body of the at least one implantable medical lead or an externalization of a conductor of the at least one implantable medical lead; and
identifying the at least one of a breach of the outer insulation of the lead body or an externalization of the conductor based on the identification of the characteristic of the second electrical signal.

17. The method of claim 16, wherein:
identifying the characteristic of the second electrical signal comprises comparing the characteristic of the second electrical signal sensed on the at least one implantable medical lead to a threshold; and
identifying the at least one of a breach of the outer insulation of the lead body or an externalization of the conductor comprises identifying the at least one of a breach of the outer insulation of the lead body or an externalization of the conductor based on the comparison.

18. The method of claim 17, wherein:
comparing the characteristic of the second electrical signal comprises comparing an amplitude of the second electrical signal sensed on the at least one implantable medical lead to a threshold amplitude; and
identifying the at least one of a breach of the outer insulation of the lead body or an externalization of the conductor comprises identifying the at least one of a breach of the outer insulation of the lead body or an externalization of the conductor based on whether the amplitude of the second electrical signal sensed on the at least one implantable medical lead is greater than the threshold amplitude.

19. The method of claim 18, wherein the threshold amplitude corresponds with an expected amplitude of the second electrical signal induced on the implantable medical lead by the first electrical signal generated by the signal generator when the implantable medical does not have the at least one of a breach of the outer insulation of the lead body or an externalization of the conductor.

20. The method of claim 16, further comprising adjusting a therapy provided by the implantable medical system in response to identifying the at least one of a breach of the outer insulation of the lead body or an externalization of the conductor.

21. The method of claim 16, wherein analyzing the second electrical signal comprises analyzing at least one of an amplitude, a waveform morphology, a frequency, a phase, a slope, and a polarity of the second electrical signal.

22. The method of claim 16, further comprising orientating the pair of electrodes to contact the body of the patient such that a vector between the at least two electrodes in contact with the body of the patient is not substantially perpendicular to a vector between an externalized conductor of the at least one implantable medical lead and an intact electrode of a sensing electrode pair.

23. The method of claim 16, wherein:
identifying the characteristic of the second electrical signal comprises identifying the characteristic of the second electrical signal that is indicative of an externalization of the conductor of the at least one implantable medical lead; and
identifying the at least one of a breach of the outer insulation of the lead body or an externalization of the conductor comprises identifying an externalization of the conductor based on the identification of the characteristic of the second electrical signal.

24. A medical device system comprising:
means for generating a first electrical signal to be delivered to a body of a patient via a pair of electrodes in contact with the body of the patient;

means for sensing a second electrical signal induced on at least one implantable medical lead by the first electrical signal;

means for identifying a characteristic of the second electrical signal that is indicative of at least one of a breach of outer insulation of a lead body of the at least one implantable medical lead or an externalization of a conductor of the at least one implantable medical lead; and means for identifying the at least one of a breach of the outer insulation of the lead body or an externalization of the conductor based on the identification of the characteristic of the second electrical signal.

25. The system of claim 24, wherein:

the means for identifying the characteristic of the second electrical signal comprises means for comparing an amplitude of the second electrical signal sensed on the at least one implantable medical lead to a threshold amplitude; and the means for identifying at least one of a breach of the outer insulation of the lead body or an externalization of the conductor bases the identification on whether the amplitude of the second electrical signal sensed on the at least one implantable medical lead is greater than the threshold amplitude.

26. The system of claim 24, wherein:

the means for identifying the characteristic of the second electrical signal comprises means for identifying the characteristic of the second electrical signal that is indicative of an externalization of the conductor of the at least one implantable medical lead; and the means for identifying the at least one of a breach of the outer insulation of the lead body or an externalization of the conductor comprises means for identifying an externalization of the conductor based on the identification of the characteristic of the second electrical signal.

* * * * *